(12) United States Patent
Day et al.

(10) Patent No.: US 9,849,200 B2
(45) Date of Patent: *Dec. 26, 2017

(54) STRONTIUM PHOSPHATE MICROPARTICLE FOR RADIOLOGICAL IMAGING AND THERAPY

(71) Applicant: MO-SCI Corporation, Rolla, MO (US)

(72) Inventors: Delbert E. Day, Rolla, MO (US); Yiyong He, Rolla, MO (US)

(73) Assignee: MO-SCI Corporation, Rolla, MO (US)

( * ) Notice: Subject to any disclaimer, the term of this patent is extended or adjusted under 35 U.S.C. 154(b) by 542 days.

This patent is subject to a terminal disclaimer.

(21) Appl. No.: 14/519,768

(22) Filed: Oct. 21, 2014

(65) Prior Publication Data

US 2015/0118495 A1 Apr. 30, 2015

Related U.S. Application Data

(63) Continuation-in-part of application No. 12/883,827, filed on Sep. 16, 2010, now Pat. No. 8,865,123.

(51) Int. Cl.
| | |
|---|---|
| A61K 51/02 | (2006.01) |
| A61K 51/12 | (2006.01) |
| C01B 25/45 | (2006.01) |
| C01B 25/32 | (2006.01) |

(52) U.S. Cl.
CPC .......... *A61K 51/02* (2013.01); *A61K 51/1244* (2013.01); *A61K 51/1251* (2013.01); *C01B 25/32* (2013.01); *C01B 25/321* (2013.01); *C01B 25/45* (2013.01); *C01P 2004/60* (2013.01); *C01P 2004/61* (2013.01); *C01P 2006/12* (2013.01); *C01P 2006/44* (2013.01); *Y10T 428/2982* (2015.01)

(58) Field of Classification Search
CPC .... A61K 51/02; A61K 51/1251; C01B 25/45; C01P 2006/44; C01P 2004/61; C01P 2006/12
See application file for complete search history.

(56) References Cited

U.S. PATENT DOCUMENTS

| | | | |
|---|---|---|---|
| 3,331,784 A | 7/1967 | Meyer et al. | |
| 3,851,044 A | 11/1974 | Adler et al. | |
| 4,339,421 A | 7/1982 | Schultess et al. | |
| 4,789,501 A | 12/1988 | Day et al. | |
| 5,011,677 A | 4/1991 | Day et al. | |
| 5,011,797 A | 4/1991 | Day et al. | |
| 5,302,369 A | 4/1994 | Day et al. | |
| 5,560,901 A | 10/1996 | Brodack et al. | |
| 5,611,833 A | 3/1997 | Brahmbhatt et al. | |
| 5,651,956 A | 7/1997 | Nosco et al. | |
| 5,690,908 A | 11/1997 | Deutsch et al. | |
| 6,165,440 A | 12/2000 | Esenaliev | |
| 6,358,531 B1 | 3/2002 | Day et al. | |
| 6,379,648 B1 | 4/2002 | Day et al. | |
| 6,455,024 B1 | 9/2002 | Glajch et al. | |
| 6,537,518 B1 | 3/2003 | Gray | |
| 6,589,549 B2 | 7/2003 | Shih et al. | |
| 6,797,704 B2 | 9/2004 | Leong et al. | |
| 7,534,448 B2 | 5/2009 | Saltzman et al. | |
| 7,768,399 B2 | 8/2010 | Hachmann et al. | |
| 7,959,900 B2 | 6/2011 | Peng et al. | |
| 8,865,123 B1 | 10/2014 | Day et al. | |
| 2004/0197264 A1 | 10/2004 | Schwarz et al. | |
| 2004/0258614 A1 | 12/2004 | Line et al. | |
| 2007/0053830 A1 | 3/2007 | Peng et al. | |
| 2008/0038190 A1 | 2/2008 | Simpson et al. | |
| 2008/0226547 A1 | 9/2008 | Larsen et al. | |
| 2009/0208428 A1 | 8/2009 | Hill et al. | |
| 2010/0055019 A1 | 3/2010 | Day et al. | |
| 2010/0160527 A1 | 6/2010 | Royer et al. | |

FOREIGN PATENT DOCUMENTS

| | | |
|---|---|---|
| CN | 1127093 A | 12/1999 |
| CN | 1640498 A | 7/2005 |
| CN | 101284161 A | 10/2008 |
| CN | 101321542 A | 12/2008 |
| EP | 1162626 A1 | 12/2001 |
| WO | 0029034 | 5/2000 |
| WO | 2005087274 | 9/2005 |
| WO | 2005/993673 A2 | 10/2005 |
| WO | 2009/064460 A2 | 5/2009 |

OTHER PUBLICATIONS

Yao, et al., "In vitro Bioactive Characteristics of Borate-based Glasses with Controllable Degradation Behavior," 2007, Journal of the American Ceramic Society.
Cast Steel: Gas Nitriding, Keyto Metals, 2009-2010. (not attributed). Turker and Ozer, Diagnostic Radiopharmaceutical Agents, Journal of Pharmaceutical Science, 29, 145-154, 2004.
Karesh, et al., Radiopharmaceuticals in Nuclear Medicine, nucmedtutorials.com, Apr. 8, 2010.
Saatchi and Hafeli, Radiolabeling of Biodegradable Polymeric Microspheres with [99mTc(C0)3]+ and in Vivo Biodistribution Evaluation using MicroSPECT/CT Imaging, Bioconjugate Chem., 2009, 20, 1209-1217.
Christoffersen, et al., "Effects of Strontium Ions on Growth and Dissolution of Hydroxyapatite and on Bone Mineral Detection," Bone, Official Journal of the International Bone and Mineral Society, vol. 20, Issue 1, pp. 47-54, Jan. 1997.
Dedhiya, et al., "Mechanism for the Retardation of the Acid Dissolution Rate of Hydroxyapatite by Strontium," Journal of Dental Research, 1973; 52; 1097.
Pan, et al., "Strontium Borate Glass: Potential Biomaterial for Bone Regeneration," Journal of the Royal Society; dol: 10.1098/rsif. 2009. 0504; Dec. 23, 2009.
Wu, "The Study of Strontium Niobium Phosphate Glass Properties and Structure," Master's Thesis, date of defense Jul. 7, 2009.
Sudarsanan and Young, "Structure of Strontium Hydroxide Phosphate, $Sr_5(PO_4)_3OH$," Act Cryst. (1972), B28, 3668.

(Continued)

*Primary Examiner* — Michael G Hartley
*Assistant Examiner* — Leah Schlientz
(74) *Attorney, Agent, or Firm* — Senniger Powers LLP

(57) ABSTRACT

This invention relates to strontium-phosphate microparticles that incorporate radioisotopes for radiation therapy and imaging.

19 Claims, 2 Drawing Sheets

(56) References Cited

OTHER PUBLICATIONS

Abstract of JP 09-165327.
Abtract of JP 09-165328.
Conzone, S. et al., Journal of Biomedical Materials Research, Part A (2008), 88A, (2), 531-542.
Office Action issued Oct. 21, 2014 in U.S. Appl. No. 14/519,587, 12 pages.
International Search Report, PCT/US2014/061597, dated Jun. 25, 2015, 5 pages.
Written Opinion, PCT/US2014/061597, dated Jun. 25, 2015, 6 pages.
Sinouh et al., "Effect of TiO2 and SrO additions on some physical properties of $33Na_2O-xSrO-xTiO_2-(50-2x)B_2O_3-17P_2O_5$ glasses", Journal of Thermal Analysis and Calorimetry, 2013, vol. 111, No. 1, pp. 401-408.
International Preliminary Report on Patentability, PCT/US2014/061597, dated May 4, 2017, 7 pages.

STRONTIUM PHOSPHATE MICROPARTICLE FOR RADIOLOGICAL IMAGING AND THERAPY

REFERENCE TO RELATED APPLICATIONS

This application is a continuation-in-part of application Ser. No. 12/883,827 filed Sep. 16, 2010 and issued Oct. 21, 2014 as U.S. Pat. No. 8,865,123.

FIELD OF THE INVENTION

The field of the present invention is radiomicroparticles for medical therapy and imaging, and particularly radioactive strontium phosphate microparticles for radiological imaging and radioisotope therapy.

BACKGROUND

In the treatment of patients with certain kinds of cancer or rheumatoid arthritis, methods are known in which radioactive particles are introduced intravascularly to a tumor site (radioembolization) or locally into the synovial fluid in a joint in order to trap the radioactive particle at a particular site for its radiation effect. Similar methods are used for imaging parts of the body, organs, tumors, and so forth.

According to this technique, a quantity of the radioactive particles are injected into a localized area of the patient to be imaged and/or treated. For imaging, gamma emitting materials are commonly used to label carriers that provide imaging of a tissue area, tumor or organ. Some of these carriers have a specific affinity for certain binding sites or biochemical targets allowing target specific or location specific uptake of the labelled carrier.

Radiological imaging of various tissues in the human body is commonly accomplished using Technetium-99m, typically by single photon emission computed tomography (SPECT). $^{99m}$-Tc is a well-known radioactive isotope used for radiodiagnostics and imaging such as SPECT. It emits detectable low level 140 keV gamma rays, has a half-life of 6 hours and decays to Tc-99 in 24 hours (93.7%). It is used for imaging and function studies of the brain, myocardium, thyroid, lungs, liver, gallbladder, kidneys, bone, blood, and tumors. It is reported to be used in over 20 million diagnostic nuclear medicine procedures each year. Positron emission tomography (PET) employs radionuclides that emit positrons, a beta-like nuclear particle that travels a few millimetres from its nucleus, collides with an electron leading to annihilation resulting in creating two photons of 511 KeV that travel in 180° opposite direction. The PET imaging system captures and registers the photons arising from the collision precisely at the same time thereby providing exceptional imaging sensitivity. PET imaging has become a valuable diagnostic imaging procedure, particularly in the oncology area and it has been reported that in the US approximately two million PET scans are performed annually. Radioisotopes commonly employed for PET imaging include fluorine-18 ($^{18}$F) that has a half-life of 109.8 minutes and gallium-68 ($^{68}$Ga) that has a half-life of 68 minutes.

Targeted radiation therapy using microparticles or microspheres is also a well-developed field radioisotope therapy. Radionuclides such as Yttrium-90 and Holmium-166 are commonly used radioactive beta emitters in microsphere radiotherapy. Polymer microspheres such as albumin, polylactic acid derivatives, and so forth, and glass microspheres, are both generally known in the medical arts for use in delivering both pharmaceuticals and radiopharmaceuticals to specific tissue sites. These microspheres are usually provided preloaded with a single radionuclide and so lack the flexibility to control dose or radionuclide depending on the patient's needs. Further, when radio micro particles are prepared in bulk, off-site by third party providers, the selection of radionuclide available for use may be limited, by the time involved in preparation and delivery.

However, a need remains for a radioactive microparticle for delivery of one or more radiopharmaceuticals and which have characteristics which will permit the microparticles to be suitable for injection into a patient for localized imaging or therapy.

BRIEF SUMMARY OF THE INVENTION

The invention provides a radio microparticle comprising crystalline strontium phosphate and at least one radioisotope suitable for radio imaging and/or radiotherapy bonded or adsorbed to the surface thereof.

The radio microparticle of the present invention is prepared by reacting a strontium-containing borate glass microparticle with a phosphate solution in amounts and for a sufficient time under suitable conditions (such as time, temperature, phosphate concentration etc.) to convert at least a portion strontium-containing borate glass at the surface to crystalline strontium phosphate, and bonding at least one radioisotope suitable for radio imaging and/or radiotherapy to the surface of said microparticle. This results in radiopaque, porous particles capable of being loaded with one or more radioisotopes and therefore being able to deliver radiation in a dose suitable for radiotherapy, or depending on the isotope chosen, for use in radiodiagnostics.

There is also provided a strontium phosphate radiomicroparticle, made by the process comprising:
a. reacting a strontium-containing borate glass microparticle with a phosphate solution such as to convert at least a portion of the strontium-containing borate glass microparticle to strontium phosphate; and
b. bonding or adsobing at least one radioisotope suitable for radioimaging and/or radiotherapy to said microparticle.

In other preferred embodiments, there are provided additional features available singularly and in combination.
In other preferred embodiments, there are provided additional features available singularly and in combination.
In one preferred process, there is provided wherein the strontium-containing borate glass microparticle is a microsphere having a diameter of about 5, 10 or 20 um to about 1000 μm.

In one preferred process, there is provided wherein the strontium phosphate microparticle has a surface area of about 90 square meters per gram or greater. The surface area may be up to about 200 square meters per gram or greater. Preferably the surface area is between about 90 to about 200 square meters per gram. In one preferred process, there is provided wherein the at least one radioisotope is a therapeutic alpha or beta-emitting radioisotope; and/or wherein the at least one radioisotope is a diagnostic proton or gamma-emitting radioisotope; and/or wherein the at least one radioisotope is a combination of a therapeutic alpha or beta-emitting radioisotope and a diagnostic proton or gamma-emitting radioisotope.

In one preferred process, there is provided wherein the step of bonding or adsorbing said at least one radioisotope suitable for radioimaging and/or radiotherapy to the strontium phosphate microparticle is prepared in situ in a clinical setting by mixing just prior to the time of administration to a patient said strontium phosphate microparticle with the at least one radioisotope suitable for radioimaging and/or radiotherapy. Thus the step of bonding the radioisotope to the strontium phosphate microparticle may be carried out just prior to the time of administration to a patient (e.g. within 6, 12 or 24 hrs)

In one preferred process, there is provided wherein the at least one radioisotope is Technetium-99m; and/or wherein the at least one radioisotope is selected from the group consisting of Technetium-99m, Indium-111 Lutetium-177, Samarium-153, Yttrium-90, Gallium-68, Fluorine-18 and combinations thereof.

In another preferred embodiment, there is provided a strontium phosphate radiomicroparticle made according to the process described herein.

In one preferred radiomicroparticle, there is provided wherein the at least one radioisotope comprises at least two different radioisotopes; and/or wherein the at least one radioisotope comprises at least three different radioisotopes.

In another preferred embodiment, there is provided a method of administering strontium-phosphate radiomicroparticles to a patient in need thereof, comprising locally delivering (for example by catheter or suitable intravenous injection) to a tissue target or organ of the patient a composition comprising strontium-phosphate microparticles with at least one radioisotope bonded or adsorbed thereto and a physiologically acceptable carrier.

In other preferred methods, there are provided additional features available singularly and in combination.

In one preferred method, there is provided wherein the at least one radioisotope is a radiodiagnostic agent; and/or wherein the at least one radioisotope is a radiotherapeutic agent; and/or wherein the at least one radioisotope comprises a radiodiagnostic agent and a radiotherapeutic agent.

In one preferred method, there is provided wherein the at least one radioisotope comprises at least two different radioisotopes; and/or wherein the at least one radioisotope comprises at least three different radioisotopes.

In one preferred method, there is provided wherein the at least one radioisotope is technetium-99m; and/or wherein the at least one radioisotope is selected from the group consisting of Technetium-99m, Indium-111, Yttrium-90, Lutetium-177, Samarium-153, Gallium-68, Fluorine-18 and combinations thereof; and/or wherein the composition also contains an additional radiotherapeutic agent.

In one preferred method, there is provided wherein the tissue target or organ is selected from the group consisting of: brain, myocardium, thyroid, lung, liver, spleen, gall bladder, kidney, bone, blood, and head and neck tumor, prostate, breast, ovarian and uterine. In one preferred method, there is provided wherein the strontium phosphate microparticles with at least one radioisotope are prepared in situ in a clinical setting by mixing just prior to the time of administration to a patient said strontium phosphate microparticle with the at least one radioisotope suitable for radioimaging and/or radiotherapy.

In another preferred embodiment, there is provided a method of obtaining a radiologic image of a tissue or organ of a patient, comprising administering (e.g. by catheter or suitable intravenous injection) to a tissue target or organ of the patient a composition comprising strontium-phosphate microparticles with at least one radiodiagnostic agent bonded or adsorbed thereto in a physiologically acceptable carrier, and obtaining the radiologic image of the tissue or organ of the patient, such as by imaging the photons or gamma radiation emitted by the radiodiagnostic agent using a suitable radionuclide imaging technique. The imaging technique may, for example be SPECT or PET.

Additional features of this method include: wherein the at least one radioisotope is a radiodiagnostic agent; wherein the radiodiagnostic agent is Technetium-99m; and wherein the tissue target or organ is selected from the group consisting of: brain, myocardium, thyroid, lung, liver, spleen, gall bladder, kidney, bone, blood, and head and neck tumor, prostate, breast, and uterine.

There is also provided microparticles, particularly microspheres, comprising crystalline strontium phosphate and having a diameter of between 5 and 1000 um (preferably 5, 10 or 20 to 200 um). Preferably such microspheres have a surface area of 90 meters square per gram or greater In other preferred embodiments, there are provided additional features available singularly and in combination, including: wherein the strontium-containing borate glass microparticle is a microsphere; wherein the strontium-containing borate glass microparticle is fully converted to a strontium phosphate microparticle through to the interior, or wherein it is partially converted to create a porous layer over an unconverted glass core; wherein the strontium-containing borate glass microparticle is between about 20 and about 40 microns in diameter; wherein the strontium-containing borate glass microparticle is between about 5 um and about 1000 um in diameter; wherein the strontium phosphate microparticle is amorphous or crystalline; wherein the strontium phosphate microparticle is a microsphere; wherein the strontium phosphate microsphere or strontium phosphate portion of the microsphere is porous; and wherein the strontium-containing borate glass microsphere is fully converted to a strontium phosphate microparticle. The strontium containing biorate glass is converted to a mineral of the Bevolite $Sr_{10}(PO_4)_6(OH)_2$ type. In some embodiments, the strontium-containing borate glass microparticle may be substantially calcium-free.

In another preferred embodiment, the at least one radioisotope is any approved radiopharmaceutical available to nuclear medicine practitioners.

DETAILED DESCRIPTION OF THE INVENTION

Figure 1:
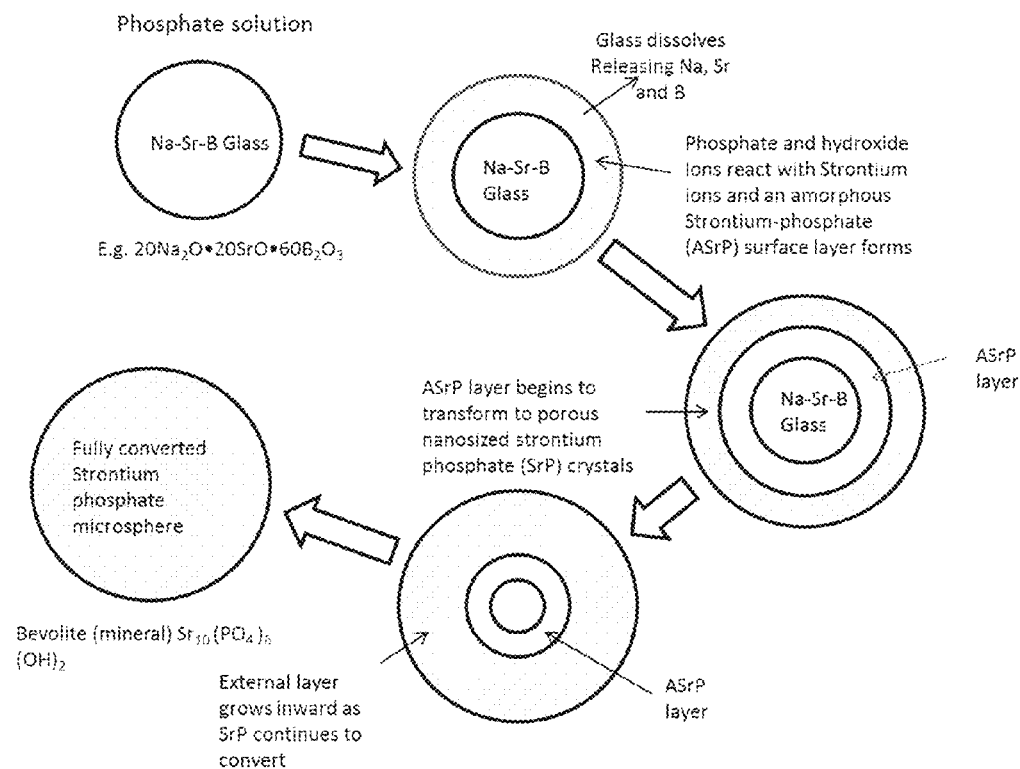
FIG. 1 illustrates the conversion of a strontium containing borate glass microsphere into a crystalline strontium phosphate microsphere
Figure 2:
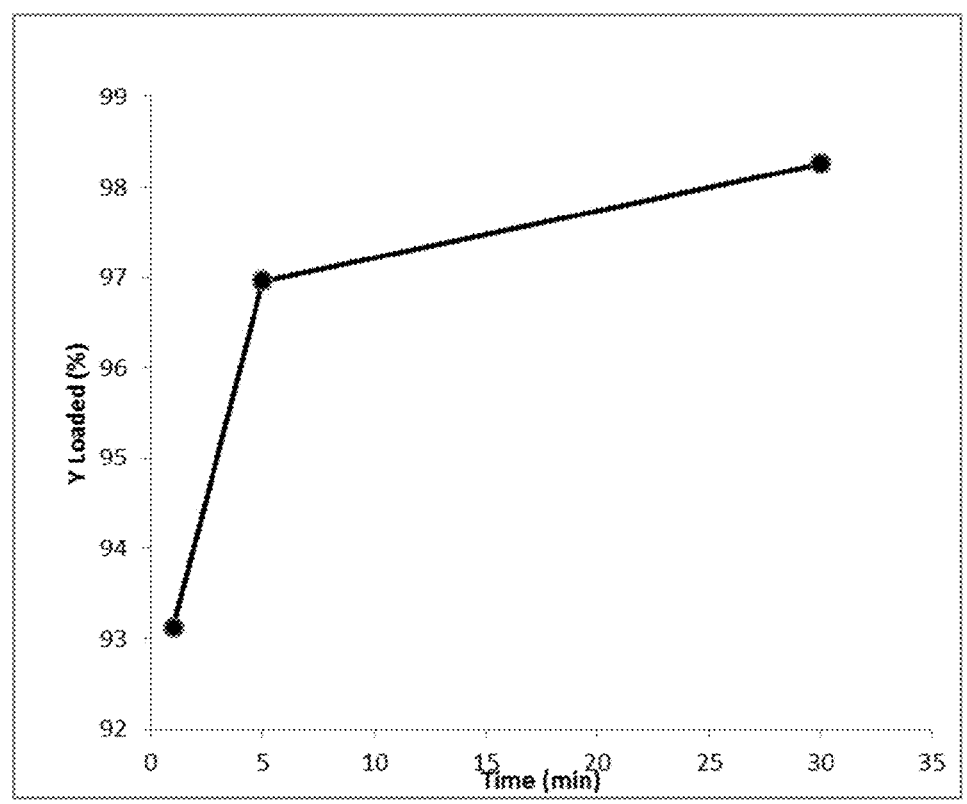
FIG. 2 shows the up-take of 90Y from a solution of 90Yttrium chloride into strontium phosphate microspheres of the invention over a period of 30 minutes.

This application is a continuation-in-part of application Ser. No. 12/883,827 filed Sep. 16, 2010 and issued Oct. 21, 2014 as U.S. Pat. No. 8,865,123, the entire disclosure of which is expressly incorporated herein by reference.

In accordance with the present invention, novel porous strontium phosphate microparticle carriers have been devised for use in the imaging and/or treatment of certain tumor bearing tissue, rheumatoid arthritis, or other diseases where nuclear medicine imaging or treatment is indicated. These carriers constitute microparticles that comprise a porous strontium-phosphate material having one or more radiopharmaceuticals bound or adsorbed to the surface. Radiodiagnostic gamma or proton emitting agents and radiotherapeutic alpha or beta emitting agents are contemplated.

Overview

The strontium phosphate radiomicroparticle of the present invention is made by reacting a strontium-containing borate glass microparticle with a phosphate solution in amounts and for a sufficient time under suitable conditions to convert the strontium-containing borate glass microparticle to a strontium phosphate microparticle, and bonding at least one radioisotope suitable for radioimaging and/or radiotherapy in a mammal to said strontium phosphate microparticle.

The phosphate solution conversion process converts a solid strontium borate glass into a porous strontium phosphate material. By manufacturing a non-radioactive solid strontium-containing borate glass microparticle of a specific diameter, the conversion results in a porous strontium phosphate microparticle of a specific diameter. Due to the substantially thorough chemical action of the phosphate solution on the borate glass, a substantially pure porous strontium phosphate material having a high surface area is achieved in the location where the phosphate solution has reacted with the borate glass.

The porosity of the resulting strontium phosphate material and the controllable size and number of the microparticles provide an excellent delivery platform for delivering compounds of interest to specific locations. Thus, the process of manufacturing of the microsphere has been divorced from the process of adding the radiolabel or radiotherapeutic. This provides nuclear medicine professionals the ability to control the radiodiagnostic and radiotherapeutic regimen by allowing, in the clinical setting, at or near the time of delivery, the decision of the type and quantity of radiopharmaceutical(s) to be incorporated into the delivery vehicle.

Advantages

Some of the advantages provided by this approach include: the ability to adsorb a radioisotope or combination of radioisotopes onto a porous microparticle, the ability to customize dose to the patient, customize imaging of the tissue, reducing time-related degradation of the activated radiopharmaceutical, and reducing exposure to medical personnel.

An additional advantage provided by this approach includes an increase in radio-opacity which provides clearer radiographic images due to the use of strontium phosphate rather than calcium apatite.

A further advantage provided by this approach includes the ability to blend two or more different radioisotopes. Further, this allows for the therapy to be able to change over time, or be customized to a particular set of circumstances.

A further advantage is the ability to use radioisotopes that have a short half life and to avoid using microparticle manufacturing processes that would vaporize certain radioisotopes such as Technetium and Rhenium.

Porosity

Importantly, the strontium phosphate microparticles achieve a porosity, or surface area, that allows for a significant amount of radioisotope to be bound. It is contemplated that surface area values of 90 square meters per gram or greater are within the scope of the present invention. The surface area may be up to 200 meters squared per gram or greater. The surface area is preferably between 90 and 200 meters squared per gram.

Significantly, prior art attempts using calcium apatite to create the microparticles have provided much lower surface area values of only 40 sq. meters per gram, or less. Further, these calcium-only microparticles demand complex manufacturing that includes a two-step process to adsorb the isotope requiring a binder, a heating step that destroys the surface area, and chemical precipitation.

These radioactive substantially spherical strontium phosphate radiomicroparticles are made by reacting a pre-made strontium-containing borate glass microparticle with a phosphate solution in amounts and for a sufficient time under suitable conditions to convert, partially or fully, the strontium-containing borate glass microparticle to an amorphous or crystalline strontium phosphate microparticle. Once the glass has been converted and the porous material is made, a radioisotope-bearing radiopharmaceutical is then adsorbed or bonded to the substantially pure strontium phosphate microparticle and is then suitable for radioimaging and/or radiotherapy in a mammal.

Phosphate Conversion

The phosphate solution conversion process converts a solid strontium borate glass microparticle into a porous strontium phosphate material that can be either amorphous or crystalline, but is preferably crystalline. Amorphous strontium phosphate converts to crystalline strontium phosphate with time. The glass can be converted completely thus forming a completely porous or even hollow microparticle. The glass can also be partially converted thus resulting in a glass core and an outer porous strontium phosphate layer, which surrounds the core and to which radioisotopes may be bound or adsorbed, as described herein. The strontium-containing borate glass microparticle may be fully converted to a strontium phosphate microparticle, or it may be partially converted to create a layer comprising strontium phosphate covering the surface of the particle and an unconverted strontium containing borate glass core. Preferably the strontium phosphate containing surface layer is at least about 0.5 um thick, but it may be at least 1, 2, 3, 4, 5, 7 or 10 um thick depending on the properties required, such as binding capacity, density etc. The conversion of the borate glass is performed by exposing it to an aqueous phosphate solution. Many different phosphate solutions are contemplated as within the scope of the present invention. One non-limiting example includes phosphate buffered saline (PBS). PBS may be prepared in many different ways. Some formulations do not contain potassium, while others contain calcium or magnesium. Generally, PBS contains the following constituents: 137 mM NaCl, 2.7 mM KCl, 10 mM sodium phosphate dibasic, 2 mM potassium phosphate monobasic and a pH of 7.4. Another non-limiting example is a 0.25 M $K_2PO_4$ solution. Non-saline phosphate solutions may be prepared using monosodium phosphate ($NaH_2PO_4$), disodium phosphate ($Na_2HPO_4$), and water, with phosphoric acid or sodium hydroxide to adjust the pH as desired. Other concentrations and types of aqueous phosphate solutions are contemplated as within the scope of the invention.

Porosity may be determined by a number of methods well known in the art, however the preferred method is nitrogen absorption. These particles are preferably not biodegradable. A biodegradable particle will, not be present in the body after 2, 4, or preferably 6 months.

Strontium

Conversion of the strontium borate glass results, at the molecular level, in a high surface-area porous material, that itself, is an agglomeration containing the strontium phosphate compound. The pores of the surface provide access to the strontium phosphate compound. When a radioisotope is mixed with the microparticles, a strong chemical bond is made with the exposed strontium phosphate compound. Without being held to any particular chemical reaction or theory, it is believed that the isotope can bind in a substitution reaction removing a phosphate [$PO_4$ group], or it may be bound into a void space or it may substitute for a strontium ion [$Sr^{+2}$].

Microparticle Size and Shape

By manufacturing a non-radioactive solid strontium-containing borate glass microparticle of a specific diameter, the size and shape of the strontium phosphate microparticle can be controlled; conversion results in a porous strontium phosphate microparticle of a specific diameter. Since the starting material is a solid strontium-containing borate glass microparticle and it becomes fully (or partially) converted to a porous strontium phosphate microparticle, the physical parameters of shape, size, diameter are dictated by the glass microparticle manufacturing process. Importantly, the size and dimension of the converted strontium microparticle are substantially the same as the size and dimension of the starting strontium borate glass microparticle. This feature provides the significant advantage of being able to control the size and dimension of the delivery vehicle itself, the porous strontium phosphate microparticle.

"Microparticle", as used herein, generally refers to a particle of a relatively small size, but not necessarily in the micron size range; the term is used in reference to particles of sizes that can be less than 50 nm to 1000 microns or greater. "Radiomicroparticle" refers to the microparticles of the present invention with one or more radioisotopes adsorbed thereon. The microparticles are preferably round spheroids having a preferred diameter of about 20 µm and above. In other preferred embodiments, the microparticles range from about 20 µm to about 200 µm, from about 30-80 µm, from about 20-40 µm, and from about 25 µm to 38 µm. In another embodiment, the diameter of the particles is from about 5 to about 100 microns, preferably from about 10 to about 50 microns. As used herein, the microparticle encompasses microspheres, microcapsules, ellipsoids, fibers, and microparticles, unless specified otherwise.

Customized Delivery

The porosity of the resulting strontium phosphate material and the controllable size and number of the microparticles provide an excellent delivery platform for delivering radiation to specific locations.

Importantly, no radioisotope is incorporated in the borate glass microparticle. Thus, the process of manufacturing of the microsphere has been divorced from the process of adding the radioisotope label or the radiotherapeutic. Prior radiomicrospheres must be manufactured as glass or biopolymer particles with the radioisotope as a homogeneous integral component of the glass or biopolymer. The present inventive approach provides a medical radiology professional the ability to control the radiodiagnostic and radiotherapeutic regimen by allowing them, in the clinical setting, to decide the type and quantity of radiopharmaceutical(s) to incorporate into the delivery vehicle. Some of the advantages of this approach include the ability to customize the dose to the patient, customize imaging of the tissue, reducing time-related degradation of the activated radiopharmaceutical, and reducing exposure to medical personnel.

Delivery of Multiple Isotopes

The combination of the significantly increased surface area and the electrical attraction of the radioisotope to the porous microparticle provides for bonding multiple radioisotopes to the microparticle. In preferred embodiments, two radioisotopes are bound. Binding a first isotope to the porous microparticle is performed using simple mixing in an appropriate solution over a pre-determined time, and then washing and eluting out the unbound isotope. This provides a composition where a radioisotope is bound to the microparticles.

Binding a second isotope to the porous microparticle is performed by simple mixing in a solution having the second isotope. Importantly, the second isotope does not displace the first isotope since the microparticles have a large surface area, and a nuclear pharmacist or other professional can take advantage of the different binding capacities of various radioisotopes to the microparticles. Thus, three and even four different radioisotopes can be bound within a single dose, or batch, of microparticles.

Method of Treatment

The invention also provides a method of administering strontium-phosphate radiomicroparticles to a patient in need thereof, comprising delivering, for example by catheter or injection, to a tissue target or organ of the patient, a composition comprising strontium-phosphate radio microparticles and a physiologically acceptable carrier.

In one preferred embodiment, the method is a method of treatment of a tumor, particularly a hyper vascular tumour. Such treatments, as described further below, may be by delivery into a blood vessel such as to lodge the particles in the vasculature (radio embolization) or by direct injection into the site. Radiomicroparticles of the invention for use in such treatments are also provided by the invention.

In other preferred methods, there are provided additional features available singularly and in combination.

In one preferred method, the tissue target or organ is selected from the group consisting of: brain, myocardium, thyroid, lung, liver, spleen, gall bladder, kidney, bone, blood, and head and neck, prostate, breast, ovarian and uterine.

Diagnosis

The invention also provides a method of obtaining a radiologic image of a tissue or organ of a patient, comprising administering to a tissue target or organ of the patient a composition containing strontium-phosphate radiomicroparticles, as described herein, and obtaining a radiologic image of the tissue or organ, typically by capturing the gamma radiation emitted by the radiomicroparticles.

Diagnostic agents comprising the radiomicroparticles of the invention are thus also provided by the invention.

In this embodiment, the radioisotope is typically a radio diagnostic agent and in one embodiment is preferably Technetium-99m for SPECT imaging and fluorine 18 or Gallium 68 for PET imaging. Typically for these methods, the radio microspheres will comprise spheres in the between about 20 and about 40 microns in diameter.

The radiologic image may be captured using any suitable nuclear imaging technique.

Further, by using radiation dosimeters which show the keV peaks of various radioisotopes, activity can be tested, and tailored to a specific therapy. For example, treatment could in one non-limiting example consist of 100 units of isotope #1 and 50 units of isotope #2.

Delivery to Tissue

The microparticles may be administered to the patient for example, through the use of catheters either alone or in combination with vasoconstricting agents or by any other means of administration that effectively causes the microparticles to become embedded in the cancerous or tumor bearing tissue. For purposes of administration, the microparticles are preferably suspended in a pharmacologically acceptable suspension medium. Preferably the suspension medium has a sufficient density or viscosity to prevent the microparticles from settling out of suspension during the administration procedure. Presently preferred liquid vehicles for suspension of the microparticles include polyvinylpyrrolidone (PVP), (such as that sold under the trade designation Plasdone K-30 and Povidone by GAF Corp), one or more contrast agents, (such as that sold under the trade designation Metrizamide by Nyegard & Co. of Oslo, Norway, or under the trade designation Renografin 76 by E.

R. Squibb & Co.) and saline, or combinations thereof. Although many contrast media provide for the adjustment of specific gravity, the addition of specific gravity adjusting components, such as dextrans (e.g. 50% dextran) may also be useful.

Types of Radioisotopes

In a preferred embodiment of the present invention, the radioisotopes/radionuclides are chosen so that when administered to the patient, the microparticles may emit alpha, beta or gamma radiation, or protons or a combination of two or more of these. The alpha or beta emitter is chosen to deliver a therapeutic intensity and therapeutic amount of short-range (e.g., a penetration of the tissue on the order of about several millimetres or less) radiation but does not emit a significant amount of unwanted radiation which could have a negative impact on healthy tissue surrounding the cancerous or tumor bearing tissue. The gamma or proton emitter is chosen to deliver a diagnostic intensity and diagnostic amount of longer-range (e.g., capable of external detection) gamma radiation, or protons, but does not emit a significant amount of unwanted radiation.

Since the radioisotopes/radionuclides may be bonded or prepared in situ just prior to delivery by a radiology professional, the type of radioisotope(s) may be chosen based on each patient's needs and diagnosis. By providing a patient-specific dosing, patient outcome is improved and side-effects are minimized. Patient data such as age, gender, weight, and pre-existing conditions are considered when determining a radiotherapeutic and/or radiodiagnostic profile. Cancer data such as tumor size, tumor type, tumor location, degree of surgical intervention and success, vascular structures within and adjacent to the area being treated, and organ involvement are also considered when determining a radiotherapeutic and/or radiodiagnostic profile.

The radioisotope Yttrium-90 which form radioisotopes having a half-life greater than about two days and less than about 30 days is one particularly preferred therapeutic radioisotope which emit therapeutic beta radiation.

For radioimaging techniques such as SPECT, the radioisotope technetium-99m is particularly preferred. For PET imaging Fluorine-18 or Gallium-68 are preferred.

The present invention includes wherein the radioisotope is radiopharmaceutical grade and is selected from the group consisting of: Actinium-225, Antimony-127, Arsenic-74, Barium-140, Bismuth-210, Californium-246, Calcium-46, Calcium-47, Carbon-11, Carbon-14, Cesium-131, Cesium-137, Chromium-51, Cobalt-57, Cobalt-58, Cobalt-60, Copper-64, Copper-67, Dysprosium-165, Erbium-169, Fluorine-18, Gallium-67, Gallium-68, Gold-198, Holmium-166, Hydrogen-3, Indium-111, Indium-113m, Iodine-123, Iodine-124, Iodine-125, Iodine-131 Diagnostic, Iodine-131 Therapeutic, Iridium-192, Iron-59, Iron-82, Krypton-81m, Lanthanum-140, Lutetium-177, Molybdenum-99, Nitrogen-13, Oxygen-15, Paladium-103, Phosphorus-32, Radon-222, Radium 223, Radium-224, Rhenium-186, Rhenium-188, Rubidium-82, Samarium-153, Selenium-75, Sodium-22, Sodium-24, Strontium-89, Technetium-99m, Thallium-201, Xenon-127, Xenon-133, Yttrium-90, Zirconium 89, and combinations thereof.

Where combinations of radioisotopes are used with the microparticles, preferred combinations of radioisotopes include the combination of one or more beta emitters with one or more gamma emitters. Examples of preferred combinations include, but are not limited, to Y-90/In-111 Y-90/Tc-99m, Y-90/Ga-68, Y-90/F-18, Y-90/Cu-64, Cu-67/Cu-64, Y-90/Lu-177, P-32/In-111, P-32/Tc-99m, P-32/Ga-68, Ho-166/In-111, Ho-166/Tc-99m, Sm-153/In-II 1, and Sm-153/Tc-99m.

Particularly preferred radioisotopes include Technetium-99m and Indium-111 (radiodiagnostic gamma emitters), Lutetium-177 (being both a beta and gamma emitter), Samarium-153 and Yttrium-90 (radiotherapeutic beta emitters) and Gallium-68 and fluorine-18 (diagnostic proton emitters), Tc-99m has been used for imaging and function studies of the brain, myocardium, thyroid, lungs, liver, gallbladder, kidneys, bone, blood, and tumors. Indium-111 pentetreotide has been used in imaging of neuroendocrine tumors that overexpress somatostatin receptors and has become standard for localization of these tumors. This radio ligand is internalized into the cell and can induce receptor-specific cytotoxicity by emission of Auger electrons. Lutetium-177 having both gamma and beta properties enables its use in imaging as well as treatment. It has a shorter radius of penetration that Y-90 which makes it an ideal candidate for radiotherapy of small tumors. Samarium-153 Lexidronam (chemical name Samarium-153-ethylene diamine tetramethylene phosphonate, abbreviated Sarnariurn-153 EDTMP, trade name Quadramet) is a complex of a radioisotope of the lanthanide element samarium with the chelator EDTM P. It has been used to treat cancer pain when cancer has spread to the bone. Once injected into a vein, it distributes throughout the body and localizes in areas where cancer has invaded the bone, allowing the beta particles (electrons) to destroy the nearby cancer cells. It is also commonly used in lung cancer, prostate cancer, breast cancer, and osteosarcoma. Yttrium-90 has been used in the treatment of various cancers including lymphoma, leukaemia, ovarian, colorectal, pancreatic, and bone cancers, and in treatment of rheumatoid arthritis by radionuclide synovectomy.

Although an attempt is made to provide an exhaustive list, it is well-known to nuclear medicine specialists that radioisotopes may be produced using a generator system like Mo—Tc or Sn/In systems, a thermal neutron reactor, a cyclotron, or fission produced. Accordingly, any radioisotopes with:functional equivalents to those listed are intended to be encompassed wherever appropriate within the scope of the present invention.

Glass Preparation

The strontium containing borate glass microspheres described herein represent a further aspect of the present invention. These microspheres are preferably not biodegradable. The microparticles of the present invention may be prepared from a homogenous mixture of powders (i.e., the batch) that is melted to form the desired glass composition. The exact chemical compounds or raw materials used for the batch is not critical so long as they provide the necessary oxides in the correct proportion for the melt composition being prepared. For instance, for making a strontium borate glass, then strontium, borate, and/or soda, powders may be used as some the batch raw materials.

Typically the strontium containing borate glass will comprise 10 or more mol % strontium oxide, but preferably 15 mol % or greater. The strontium containing borate glass may comprise up to 25 mol % strontium oxide, but more preferably 20±5 mol % strontium oxide.

The present invention therefore provides a strontium containing borate glass microsphere, comprising 10 or more mol % strontium oxide and having a diameter of between 5 and 1000 microns.

Typically the strontium containing borate glass will comprise 10 mol % or more sodium oxide, preferably 15 mol % or more. Preferably the strontium containing borate glass will comprise up to 30 mol % sodium oxide. Preferably the strontium containing borate glass will comprise 20±5 or 20±10 mol % sodium oxide. Up to one quarter of the sodium oxide portion of the glass may be replaced by lithium oxide or potassium oxide (or a combination of the two).

Typically the strontium containing borate glass will comprise at least 50% boron oxide, preferably the strontium containing borate glass will comprise at least 60% boron oxide, preferably the strontium containing borate glass will comprise up to 70% boron oxide. Preferably the strontium containing borate glass will comprise 60±10 mol % boron oxide.

Typical compositions suitable for preparing the batch are given below, although it is to be understood that these should not be considered to be limiting; starting glasses having a wide range of compositions can be used so long as they contain a source of strontium oxide (from the glass) and phosphate, which may be from the starting glass or may be present in the solution in which the glass is being reacted. The general compositions given below assume that the starting glass composition is being reacted in a solution that is the source of phosphate to form the strontium phosphate particle.

A typical composition comprises:

20±10 mol % $Na_2O$ which may contain up to 25% of $Li_2O$ or $K_2O$ or a combination thereof, on a molar basis, 20±5 mol % SrO, up to one quarter of which may be substituted by an alternative radiopaque oxide, such as barium, calcium manganese or cobalt oxides.

60±10 mol % $B_2O_3$; and 0-5 mol % of other oxides.

An example composition is 20:20:60 mol % $Na_2O$:SrO:$B_2O_3$.

Thus the composition can be modified by varying the soda content by up to plus/minus 5 or 10 mol %, and or the boron oxide content by plus/minus 10 mol %. It is also possible to substitute up to 5 mol % $Li_2O$ or $K_2O$ (or a combination of the two) for a portion of the soda. It is also possible to substitute small amounts of $P_2O_5$ (say up to 5 mol %) for a portion of the $B_2O_3$. A few (up to 5) mol % of a wide range of other oxides can be substituted into the base glass composition for various specific purposes such as varying the melting temperature or the conversion reaction rate, modifying the radio-opacity, etc. If needed, the SrO could be replaced partially (up to 5 mol % of the 20) by barium oxide, calcium oxide, manganese oxide or cobalt oxide (eg CO) or a combination thereof.

All percentages herein are mol % unless indicated or inherently otherwise. While the materials are described as containing various oxides and other components by molar %, those skilled in the art understand that in the final glass or crystalline composition, the compounds are dissociated, and the specific compounds are not separately identifiable or even necessarily separately present. Nonetheless, it is conventional in the art to refer to the final composition as containing a given % of the individual compounds, so that is done here. So from this perspective, the compositions herein are on an equivalent basis.

The purity of each raw material is preferably greater than 99.9%. After either dry or wet mixing of the powders to achieve a homogeneous mixture, the mixture may be placed in a platinum crucible for melting. High purity alumina crucibles can also be used if at least small amounts of alumina can be tolerated in the glass being made. The crucibles containing the powdered batch are then placed in an electric furnace which is heated 1000° C. to 1600° C., depending upon the composition. In this temperature range, the batch melts to form a liquid which is stirred several times to improve its chemical homogeneity. The melt should remain at 1000° C. to 1600° C., until all solid material in the batch is totally dissolved, usually 4-10 hours being sufficient. Significantly, by not incorporating the radioisotope into the melt, no radioisotope can be vaporized, thus avoiding a radiation hazard.

Another advantage of the invention is the ability to use radioisotopes that have a shorter half-life. For example, Tc-99m (Technetium-99m) cannot be made part of the glass, i.e. the half-life may often be too short to be useful when it is incorporated as part of certain homogeneous glass-radioisotope compositions. Additionally, the ability to use radioisotopes that would otherwise be destroyed or degrade by the glass-melt process. For example, trying to incorporate Technetium or Rhodium into a melt would vaporize the Technetium or Rhodium.

When melting and stirring is complete, the crucible is removed from the furnace and the melt is quickly quenched to a glass by pouring the melt onto a cold steel plate or into clean, distilled water. This procedure breaks the glass into fragments, which aids and simplifies crushing the glass to a fine powder. The powder is then sized and spheroidized for use.

Spheroidizing

To obtain spheroid microparticles having a diameter in the desired range of micrometres, the glass is processed using varying techniques such as grinding and passing through mesh sieves of the desired size, where the glass particles may be formed into spheroids by passing the sized particles through a gas/oxygen flame where they are melted and a spherical liquid droplet is formed by surface tension. A vibratory feeder located above the gas/oxygen burner slowly vibrates the powder into a vertical tube that guides the falling powder into the flame at a typical rate of 5-25 gm/hr. The flame is directed into a metal container which catches the spheroidized particles as they are expelled from the flame. The droplets are rapidly cooled before they touch any solid object so that, their spherical shape is retained in the solid product.

After spheroidization, the glass spheres are preferably collected and rescreened based upon size. As a non-limiting example, when the microparticles are intended to be used in the treatment of liver cancer, the fraction less than 30 and greater than 20 micrometres in diameter is recovered since this is a desirable size for use in the human liver. After screening, the −30/+20 microparticles are examined with an optical microscope and are then washed with a weak acid (HCl, for example), filtered, and washed several times with reagent grade acetone. The washed spheres are then heated in a furnace in air to 500-600° C. for 2-6 hours to destroy any organic material.

The final step is to examine a representative sample spheres in a scanning electron microscope to evaluate the size range and shape of the spheres. The quantity of undersize spheres is determined along with the concentration of non-spherical particles. The composition of the spheres can be checked by energy dispersive x-ray analysis to confirm that the composition is correct and that there is an absence of chemical contamination.

The glass microparticles are then ready for phosphate conversion, bonding with radionuclide, and subsequent administration to the patient.

In accordance with the present invention, the above processing steps are merely exemplary and do not in any way limit the present invention. Similarly, the present invention is not limited to glass microparticles having a size described above; the size of the microparticles of the present invention may be varied according to the application.

Types of Cancers

The microparticles of the present invention may be used in a variety of clinical situations for which internal radiation therapy is indicated. These include, for example the treatment of Tumors and the treatment of arthritis.

The treatment of both benign and cancerous tumors is contemplated. Tumors may be treated, for example, by selective internal radiation therapy (SIRT) for i.a. hypervascular tumors or other tumors of areas that have favorable vasculature, including the liver (liver tumors include, for example, hepatocellular carcinomas or metastatic disease arising from other tissues, such as colorectal cancers), spleen, brain, kidney, head & neck, uterine, ovarian and prostate. The microparticles may also be used for imaging, including a Liver/Spleen Scan—for tumors, cysts or hepatocellular disease; a Brain Scan—for tumors, trauma, or dementia; a Tumor Scan for malignant tumors or metastatic disease of the Kidney, Head & Neck, Uterine/Gynaecologicals; and any Scan or Therapy having favorable vasculature for this approach.

One radionuclide imaging technique contemplated as within the scope of the invention is single photon emission computed tomography (SPECT) a further technique contemplated is PET.

Since most organs, besides the liver, have only one blood vessel that feeds it, administration may be performed by delivery to that main feeder artery and allowing the microparticles to lodge in the capillary bed since they are too large to move through the capillary. The liver may require a specialized delivery regimen. In another embodiment, the vessel that feeds the tumor may be identified, and this artery is used to deliver the microparticles in a more local fashion.

EXAMPLES

Example 1

Preparation of Strontium Phosphate Microspheres

Strontium containing borate glass microspheres were prepared from a batch comprising 20 mol % $Na_2O$, 20 mol % SrO and 60 mol % $Ba_2O_3$ as described above. The microspheres ranged in size from 44 to 105 microns.

The microspheres were reacted with 0.25 molar $K_2HPO_4$ solution (pH=12) for 1 h, 6 h, and 72 hrs at 85° C. After rinsing and drying, the surface area was measured by nitrogen absorption using a Micromeretics Tristar 3000 device. Multiple samples were measured and averaged. The measured surface area was 10, 93, and 72 $m^2/gm$, respectively.

Example 2

Loading Strontium Phosphate Microspheres with Radioisotopes

A solution of 5 ug yttrium (Y-90) chloride in 0.5 ml of 0.05N HCl was added to 15 mg of microspheres and incubated for 30 minutes. The amount of yttrium loaded into the microspheres was determined at 1, 5 and 30 minutes in 5 replicates and averaged. Up-take of the yttrium with time is shown in FIG. 1.

As various changes could be made in the above methods and products, without departing from the scope of the invention, it is intended that all matter contained in the above description or shown in any accompanying drawings shall be interpreted as illustrative and not in a limiting sense. Any references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

The invention claimed is:

1. A radio microparticle comprising:
crystalline strontium phosphate and at least one radioisotope suitable for radio imaging and/or radiotherapy bonded or adsorbed to the surface thereof, wherein the microparticle has a surface area of greater than 90 square meters per gram.

2. The radio microparticle of claim 1, having a surface area of greater than about 90 square meters per gram up to about 200 square meters per gram.

3. The radio microparticle of claim 1 which is a microsphere.

4. The radio microparticle of claim 2 having a diameter of 5 μm to 1000 μm.

5. The radio microparticle of claim 1, wherein the radioisotope bonded or adsorbed to the surface is a therapeutic alpha or beta-emitting radioisotope.

6. The radio microparticle of claim 1, wherein the radioisotope bonded or adsorbed to the surface is a diagnostic positron or gamma-emitting radioisotope.

7. The radio microparticle of claim 1, wherein the radioisotope bonded or adsorbed to the surface comprises a combination of a therapeutic alpha or beta-emitting radioisotope and a diagnostic gamma or positron-emitting radioisotope.

8. The radio microparticle of claim 1, wherein the radioisotope bonded or adsorbed to the surface is Technetium-99m.

9. The radio microparticle of claim 1, wherein the radioisotope bonded or adsorbed to the surface is selected from the group consisting of Technetium-99m, Indium-111, Lutetium-177, Samarium-153, Yttrium-90, Holmium-166, Gallium-68, Fluorine-18 and combinations thereof.

10. The radio microparticle of claim 1, having at least two different radioisotopes bonded or adsorbed to the surface.

11. A process for the preparation of a radio microparticle, comprising:
(i) reacting a strontium-containing borate glass microparticle with a phosphate solution such as to convert at least a portion of the strontium-containing borate glass to crystalline strontium phosphate; and
(ii) bonding or adsorbing at least one radioisotope suitable for radio imaging and/or radiotherapy to said strontium phosphate microparticle by bringing the microparticle into contact with a solution containing the radioisotope.

12. A process according to claim 11, wherein the radioisotope is selected from the group consisting of Technetium-99m, Gallium 68, Holmium-166, Fluorine-18, Indium-111, Yttrium-90, Lutetium-177, Samarium-153, and combinations thereof.

13. A method of administering a radio microparticle to a patient in need thereof, comprising:

locally delivering the radio microparticle in a physiologically acceptable carrier to a tissue target or organ of the patient, wherein the radio microparticle comprises crystalline strontium phosphate and at least one radioisotope suitable for radio imaging and/or radiotherapy bonded or adsorbed to the surface thereof, wherein the microparticle has a surface area of greater than 90 square meters per gram.

14. The method of claim 13 wherein the microparticle is a microsphere.

15. The method of claim 13 wherein the crystalline strontium phosphate microparticles have a surface area of greater than 90 square meters per gram up to about 200 square meters per gram.

16. The method of claim 13 wherein the radioisotope bonded or adsorbed to the surface is a radio diagnostic agent.

17. The method of claim 13 wherein the radioisotope bonded or adsorbed to the surface is a radio therapeutic agent.

18. The method of claim 13, wherein the radioisotope bonded or adsorbed to the surface comprises a radio diagnostic agent and a radio therapeutic agent.

19. A method of obtaining a radiologic image of a tissue or organ of a patient, comprising:

administering a radio microparticle in a physiologically acceptable carrier to a tissue target or organ of the patient, and obtaining the radiologic image of the tissue or organ of the patient;

wherein the radio microparticle comprises crystalline strontium phosphate and at least one radioisotope suitable for radio imaging bonded or adsorbed to the surface thereof, wherein the microparticle has a surface area of greater than 90 square meters per gram.

* * * * *